(12) United States Patent
Gagnon

(10) Patent No.: US 7,375,337 B2
(45) Date of Patent: May 20, 2008

(54) CONSTANT RADIUS SINGLE PHOTON EMISSION TOMOGRAPHY

(75) Inventor: Daniel Gagnon, Twinsburg, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 183 days.

(21) Appl. No.: 10/541,559

(22) PCT Filed: Dec. 19, 2003

(86) PCT No.: PCT/IB03/06242

§ 371 (c)(1), (2), (4) Date: Jul. 6, 2005

(87) PCT Pub. No.: WO2004/061477

PCT Pub. Date: Jul. 22, 2004

(65) Prior Publication Data

US 2006/0124855 A1    Jun. 15, 2006

Related U.S. Application Data

(60) Provisional application No. 60/438,222, filed on Jan. 6, 2003.

(51) Int. Cl.
*G01T 1/164* (2006.01)
*G01T 1/166* (2006.01)

(52) U.S. Cl. .............................. 250/363.08; 250/363.05
(58) Field of Classification Search ............. 250/363.1, 250/363.08, 363.05; D24/158, 159
See application file for complete search history.

(56) References Cited

U.S. PATENT DOCUMENTS

| 4,651,007 A | * | 3/1987 | Perusek et al. ........ 250/363.08 |
| 5,055,687 A | * | 10/1991 | Ichihara .................. 250/363.09 |
| 5,376,795 A | | 12/1994 | Hasegawa et al. |
| 5,391,877 A | | 2/1995 | Marks |
| 5,569,924 A | * | 10/1996 | Plummer ................ 250/363.05 |
| 5,742,060 A | | 4/1998 | Ashburn ................ 250/370.09 |
| 6,147,352 A | * | 11/2000 | Ashburn ................ 250/363.05 |
| 6,177,675 B1 | * | 1/2001 | Gagnon et al. .......... 250/363.1 |
| 6,303,935 B1 | * | 10/2001 | Engdahl et al. ........ 250/363.03 |
| 6,448,559 B1 | | 9/2002 | Saoudi et al. ................ 250/367 |
| 2004/0022350 A1 | * | 2/2004 | Gregerson et al. ............ 378/15 |

FOREIGN PATENT DOCUMENTS

EP     1 008 865 A2   6/2000
WO    WO 00/75691 A1   12/2000

* cited by examiner

*Primary Examiner*—David P. Porta
*Assistant Examiner*—Mindy Vu

(57) ABSTRACT

A nuclear camera (10) includes four or more gamma detectors (20, 20', 20", 201, 202, 203, 204, 205, 206) arranged or, a generally circular rotatable gantry (12, 12', 12", 12''') around an imaging region that emits emission radiation. The gamma detectors are each disposed at a fixed equal distance (R, R2, R3, R5) from an imaging isocenter (22, 22', 22", 22''') to rotate in a fixed radius circular orbit. Each gamma detector includes a radiation sensitive surface (72) that responds to the emission radiation and a slat collimator (70) that spins about an axis 88. Resolution and sensitivity at the fixed radius are selected by selecting collimator slat height (Wz) and spacing (G) and radiation sensitive surface width (Cy). The gamma detectors and rotating gantry are enclosed in an optically opaque toroidal housing (14) that defines a generally circular bore (16) that admits imaging subjects over a range of sizes.

23 Claims, 6 Drawing Sheets

CONSTANT RADIUS SINGLE PHOTON EMISSION TOMOGRAPHY

CROSS REFERENCE TO RELATED APPLICATIONS

This application claims the benefit of U.S. provisional application Ser. No. 60/438,222 filed Jan. 6, 2003, which is incorporated herein by reference.

The following relates to the diagnostic imaging arts. It particularly relates to single photon emission computed tomography (SPECT) imaging, and will be described with particular reference thereto. However, it may find application in other diagnostic imaging modalities.

Nuclear cameras typically employ one to three gamma detectors mounted on a linear positioning element that is in turn mounted to a rotating gantry. The rotating gantry moves the gamma detector angularly about the region of interest, while the linear positioning element moves the gamma detector radially toward or away from a region of interest to produce a conformal non-circular orbit that closely follows external contours of an imaging subject. In another arrangement, the gamma detectors are mounted on robotic arms that provide both rotational and radial detector movement to effect conformal non-circular orbiting.

Each gamma detector includes a scintillator that is viewed by an array of photomultiplier tubes. A radiation particle strikes the scintillator and produces a flash of light. Nearby photomultiplier tubes detect the resultant scintillation event. The particle energy and position on the detector are computed based on the photomultiplier tube outputs. A collimator, which is typically a lead plate with an array of bores, is mounted on the gamma detector between the scintillation crystal and the imaged subject to define linear projection views. A detector of this type isolates a scintillation event as originating along a ray or line of view, or more precisely along a narrow-angle cone of view, defined by the axis of the collimator bore.

Another type of gamma detector employs a slat collimator. The slat collimator includes generally parallel collimating slats that define plane integral projection views. Sensitivity is improved by receiving radiation over a band rather than a narrow-angle cone. Some slat-collimated gamma detectors employ semiconductor-based radiation detectors, such as a cadmium zinc telluride (CZT) detectors. To enable spatial location along the bands to be resolved, the slats are spun or rotated during imaging about an axis transverse to the detector face, so that plane integral projections over at least 180°, and preferably 360°, of planar orientations are collected for each gantry angular view. Slat-collimated detectors, defining planes of activity instead on lines of activity, have certain advantages including improved signal sensitivity.

As the gamma detectors conformally orbit the imaging subject, linear projection data is acquired over an angular range of projection views, which are then reconstructed into a three-dimensional image. For medical imaging, a radiopharmaceutical or radioisotope such as $^{99m}Tc$ or $^{201}Tl$ is introduced into the subject. The radioisotope distributes over the circulatory system or accumulates in an organ of interest whose image is to be produced. To minimize radiation exposure of the subject, the dose of administered radiopharmaceutical and its associated half-life are limited. This in turn leads to low radiation signal strength, low signal-to-noise ratios, and temporally limited imaging windows.

To counteract these signal limitations, special attention should be given to optimizing the number of collected counts, that is, the sensitivity, as well as their quality, that is, spatial resolution. Non-circular contoured orbits of the gamma detectors about the subject substantially improves resolution and sensitivity by minimizing a distance between each gamma detector and the imaging subject.

However, contoured non-circular gamma detector orbits have certain disadvantages. Determining the precise contoured orbit, which is subject-specific, increases imaging preparation time. The number of gamma detectors on the gantry is generally limited by the conformal orbiting to three or fewer detectors. A larger number of detectors is not readily simultaneously conformally arranged in close proximity to the imaging subject. Additionally, contoured movement of large gamma detector heads in close proximity to a human imaging subject is intimidating, particularly for head scans. Conformal orbiting also precludes shielding of the moving parts from the subject's view using a gantry enclosure or gamma camera housing. Image reconstruction is also complicated by conformal orbiting, since non-circular orbiting destroys advantageous spatial symmetries, adds a radius dependency to the data, and thus increases image reconstruction complexity and time.

The present invention contemplates an improved apparatus and method that overcomes the aforementioned limitations and others.

According to one aspect, a nuclear camera is disclosed. A rotatable gantry defines a gantry rotation axis and an imaging isocenter. A gamma detector is arranged on the rotating gantry at a fixed radial distance from the imaging isocenter. The gamma detector includes a radiation-sensitive surface and a collimator that collimates incoming radiation.

According to another aspect, a nuclear camera is disclosed. At least one, up to six or more, but optimally four SPECT radiation detectors are rotatably arranged around an imaging region to receive emission radiation. The radiation detectors are each disposed an equal distance from an imaging isocenter. The radiation detectors each include a radiation-sensitive surface that responds to the first emission radiation. A slat collimator is disposed on each radiation detector between the radiation detector and the imaging region to provide planar collimation of incoming first emission radiation. A means is provided for spinning the collimator and radiation-sensitive surface of each SPECT radiation detector about a detector axis.

According to yet another aspect, a radiological imaging method is provided. At least one radiation detector is circularly orbited about an imaging volume at a fixed radial distance from a first axis of rotation through the imaging volume. Radiation from the imaging volume is detected at a generally planar radiation-sensitive region of the radiation detector. The radiation-sensitive region faces the imaging volume during the fixed radius circular orbiting.

One advantage resides in elimination of the detector orbit-contouring step in a nuclear imaging session.

Another advantage resides in providing four or more simultaneously operating gamma detectors on a single rotating nuclear camera gantry.

Yet another advantage resides in inclusion of an enclosing gantry housing surrounding a rotating nuclear camera gantry that protects moving parts such as the rotating gantry and the gamma detectors, and that blocks the moving parts from view of the imaging subject and making the nuclear imaging device comport in aspect, shape, and size with other medical imaging devices such as PET, CT, or MRI.

Still yet another advantage resides in providing imaging using a circular orbit that has a high degree of symmetry which can be used to simplify image reconstruction processing and reduce image reconstruction time.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
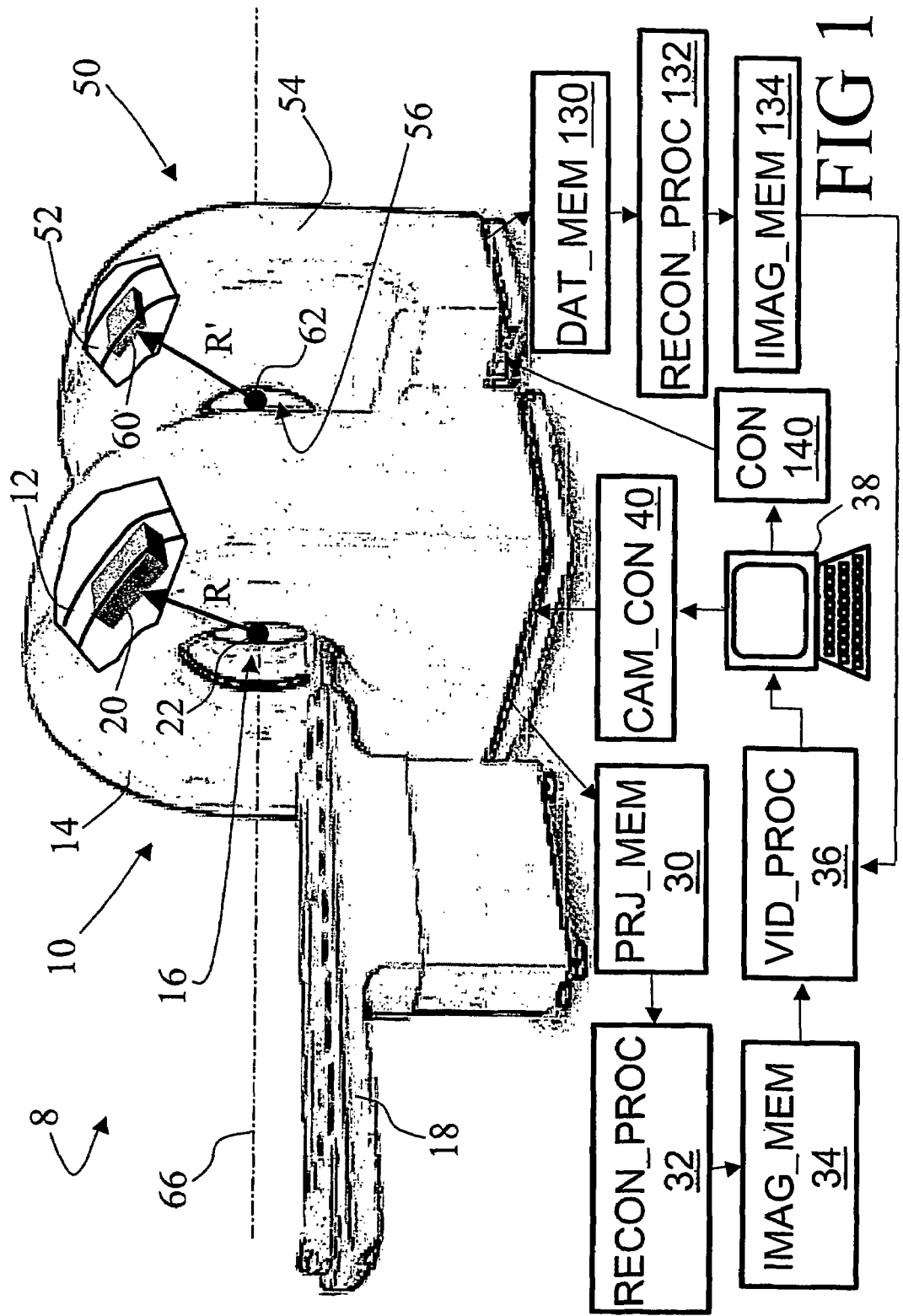
FIG. 1 shows a perspective view of a multiple imaging modality radiological imaging apparatus including a gamma camera with gamma detectors that orbit an imaging region on an enclosed gantry at a constant circular viewing radius.
Figure 3:
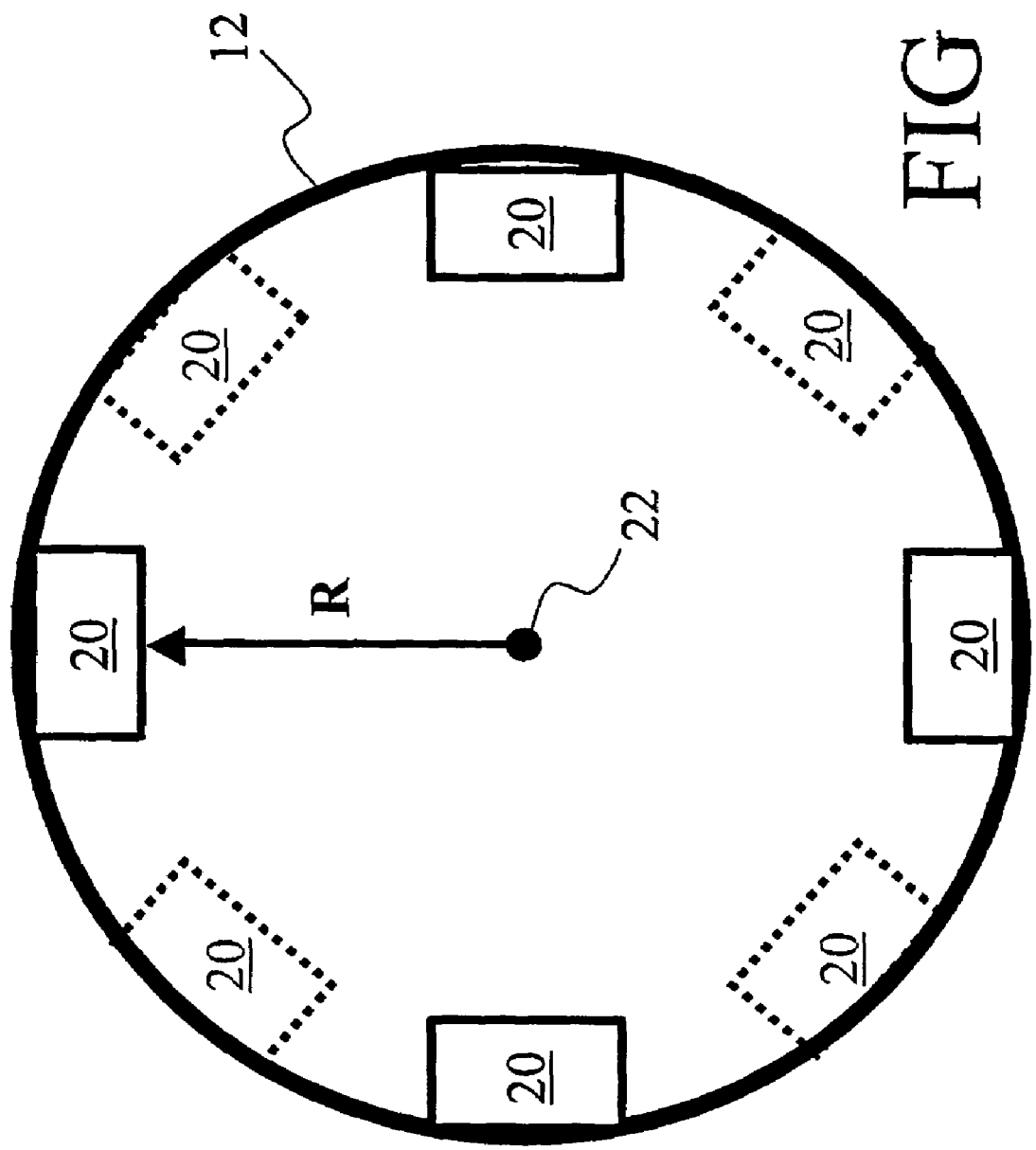

FIG. 3 diagrammatically shows arrangement of four gamma detectors at a constant viewing radius on the circular gantry of the gamma camera of FIG. 1.

Figure 4:
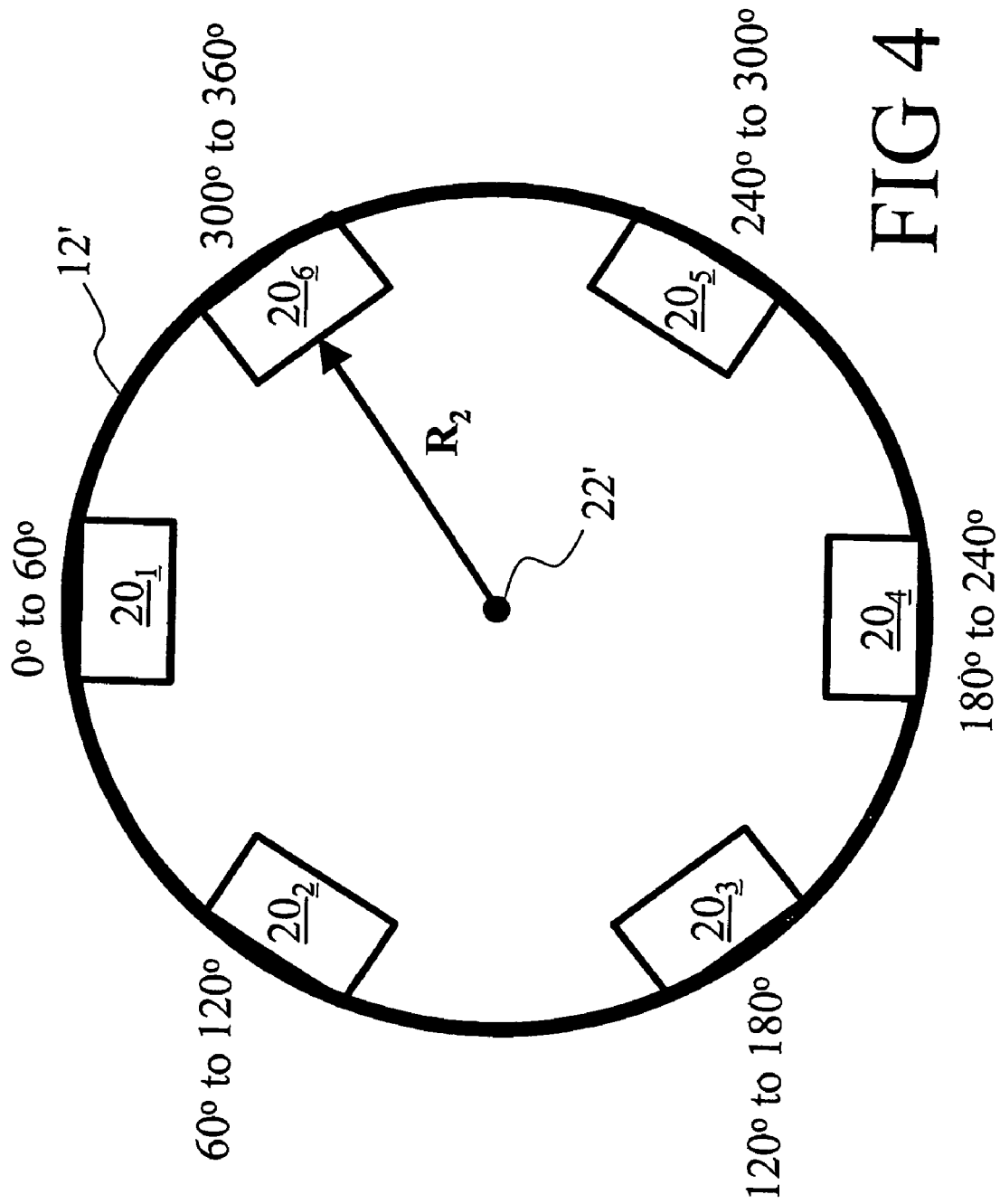

FIG. 4 diagrammatically shows six slat-collimated gamma detectors on a single constant-radius gantry, in which each of the slat-collimated gamma detectors acquires data over a selected sub-set of slat angular orientations.

Figure 5:
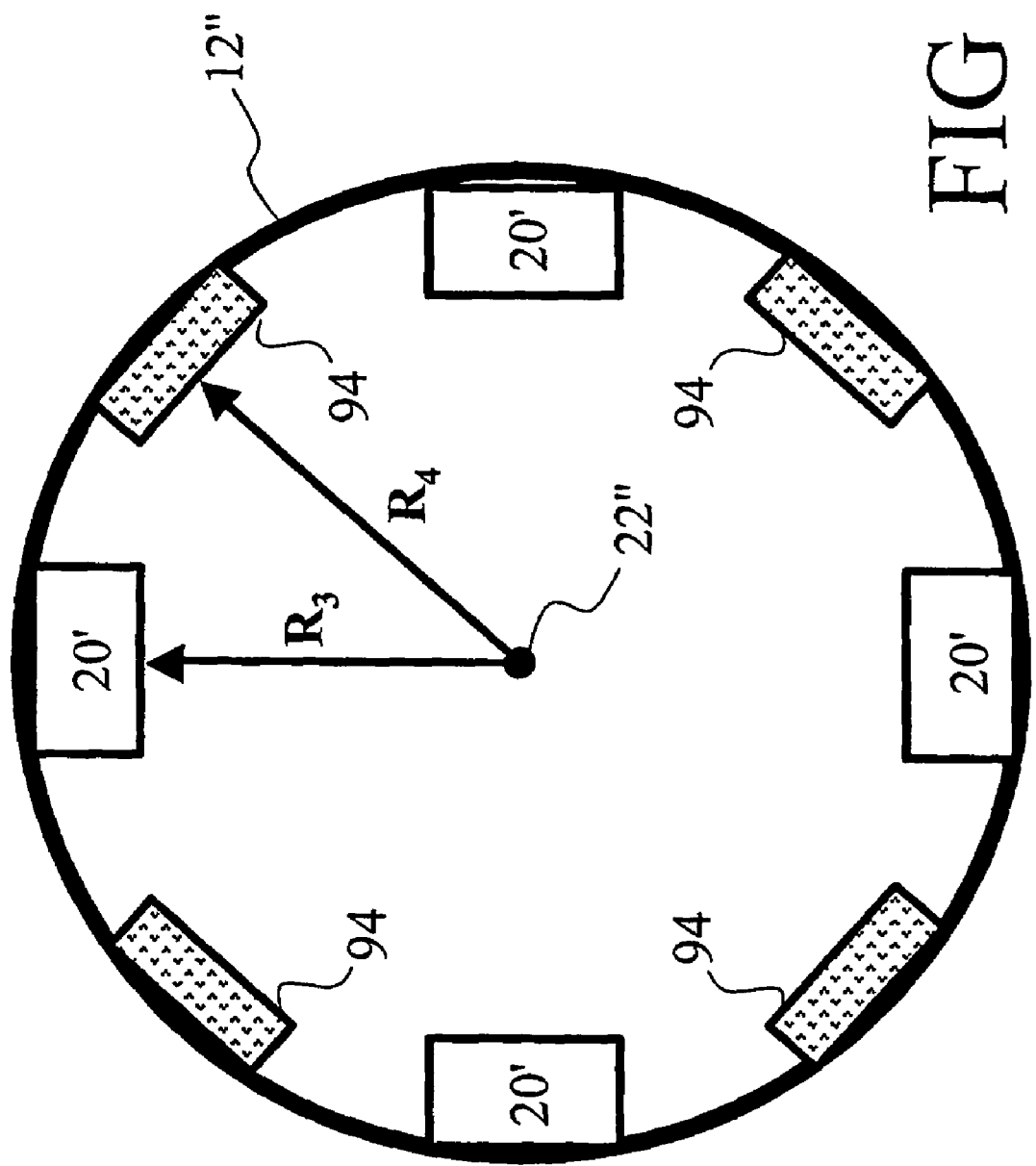

FIG. 5 diagrammatically shows a single-gantry SPECT/PET system.

Figure 6:
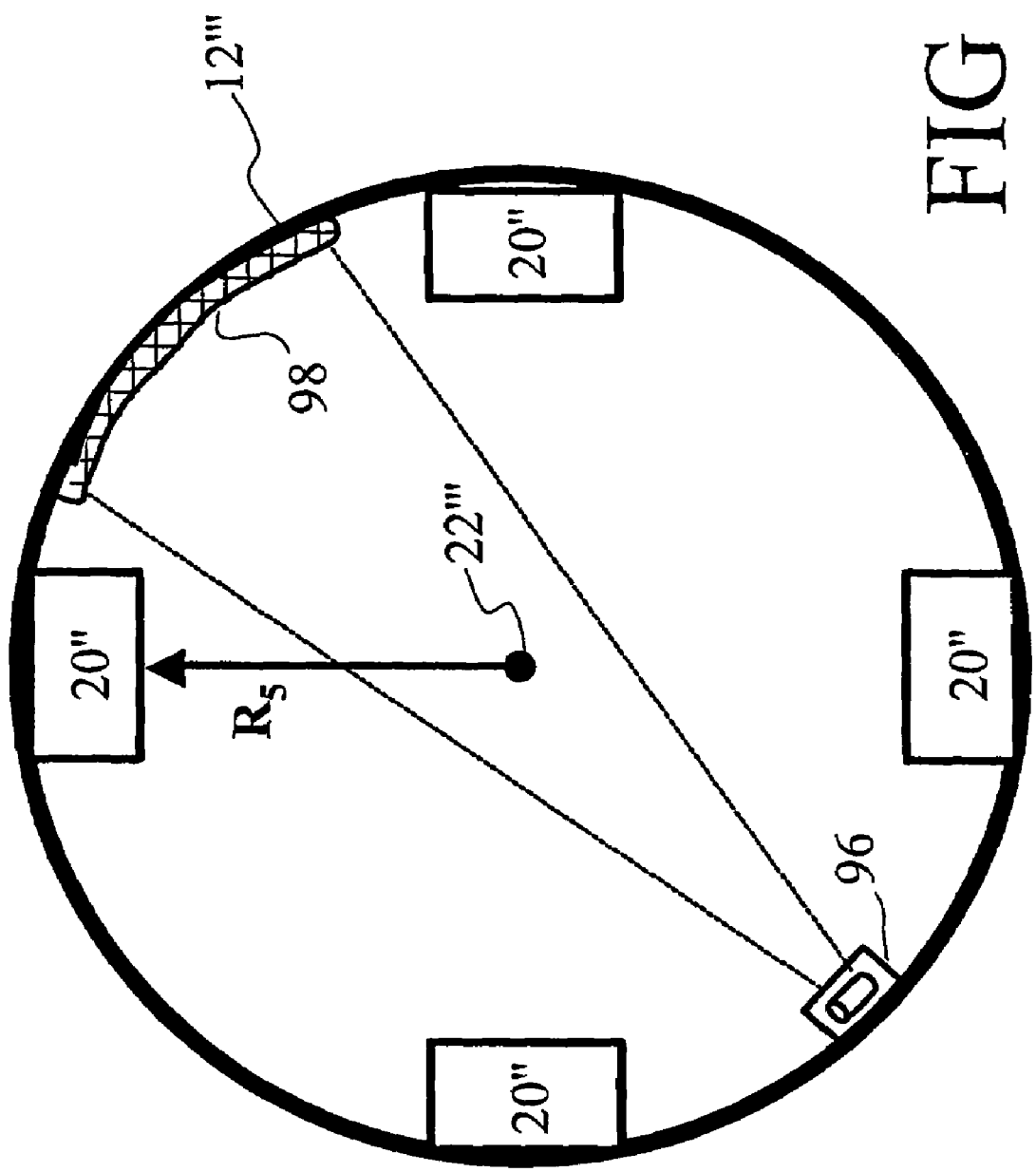

FIG. 6 diagrammatically shows a single-gantry SPECT/CT system.

With reference to FIG. 1, a multiple imaging modality radiological imaging system 8 is shown. A nuclear camera 10 includes a generally circular rotatable gantry 12 disposed in a generally toroidal stationary housing 14. The housing 14 defines a stationary generally cylindrical bore 16 inside of which an imaging subject is disposed. The housing portion that defines the stationary bore 16 is optically opaque, but generally transmissive for gamma radiation toward the bore. An imaging subject is moved into the bore 16 using a subject support couch 18. At least one gamma detector 20 (shown by partial cutaway of the enclosing housing 14) is disposed on the rotating gantry 12 and rotates therewith.

The gamma detector 20 rotates in a circular orbit of viewing radius R about an isocenter 22 of an imaging region inside the bore 16. However, a human subject disposed in the bore 16 is prevented by the housing 14 from observing the moving components of the gamma camera 10, such as the gantry 12 and gamma detector or detectors 20, because the housing 14 is optically opaque. Moreover, the circular gamma detector viewing orbit radius R is substantially larger than a minimum radius of a conformal non-circular gamma detector orbit of the type heretofore used in nuclear imaging. This allows the bore 16 to be made large enough to admit subjects of varying sizes. For medical imaging, the bore 16 is preferably large enough to admit a human subject of substantially any size, e.g. a 60 cm diameter.

With continuing reference to FIG. 1, the radiation detector or detectors 20 of the gamma camera 10 acquire plane integral projection views that are stored in a projection memory 30. The plane integral projection views are processed by a reconstruction processor 32 to reconstruct a three-dimensional image representation of the imaging region. One suitable reconstruction employs an inverse Radon transform. The reconstructed image is stored in an image memory 34.

The reconstructed image is processed by a video processor 36 and displayed on a user interface 38 for review by a radiologist or other user. The user interface 38 preferably includes a high resolution video display, a keyboard, a mouse or other pointing device, and the like. The reconstructed image can also be processed by a printer driver and printed, communicated over a hospital network or the Internet, or otherwise manipulated. Preferably, the user interface 38 also enables the radiologist or other user to operate a camera controller 40 to configure the nuclear camera 10, initiate and control data acquisition using the camera 10, and the like.

For exemplary medical imaging by single photon emission computed tomography (SPECT), a human subject is administered a suitable radiopharmaceutical or radioisotope such as $^{99m}$Tc or $^{201}$Tl prior to imaging. The radiopharmaceutical is tailored to concentrate in an organ of interest, or in the blood stream, or in another region of clinical interest. The radiopharmaceutical emits a low level of radiation, which the gamma detector or detectors 20 receive when the patient is inserted into the bore 16. The gamma camera 10 acquires projection views over 180°, 360°, or another selected angular range of viewing angles as the rotating gantry 12 moves the gamma detector- or detectors 20 around the imaging region.

Optionally, the radiological imaging apparatus 8 includes a second imaging modality apparatus 50, such as a positron emission tomography (PET) scanner, a computed tomography (CT) scanner, or a second nuclear camera A second generally circular rotatable gantry 52 is disposed in a second generally toroidal stationary housing 54. The stationary housing 54 defines a second generally cylindrical bore 56. For imaging using the second imaging modality apparatus 50, the subject support couch 18 extends to insert the subject into the second bore 56. At least one suitable radiation detector 60 (shown by partial cutaway of the enclosing housing 54) is mounted on the second rotatable gantry 52 and rotates therewith at a fixed viewing radius R' relative to an isocenter 62 of a second imaging region defined by the second bore 56. The fixed viewing radius R' may be the same or different from the fixed viewing radius R of the gamma detector or detectors 20.

For PET imaging, at least two radiation detectors are mounted and configured to perform coincidence gamma ray detection. For CT imaging, an x-ray source generates an x-ray beam that passes through the isocenter 62 and is detected by an x-ray detector array. The second imaging modality apparatus 50 also includes a data memory 130, image reconstruction processing components 132, and an image memory 134 which correspond to the components 30, 32, 34. The video processor 36 adds a spatial offset corresponding to the distance between the gantries and combines the reconstructed images for display. Optionally, data from the two imaging modalities can be combined prior to reconstruction. Preferably, the user interface 38 communicates with a controller 140 for the second gantry 50. Optionally, the memory components 30, 34 can be partitioned or otherwise configured to store data produced by each apparatus 10, 50, and a single reconstruction processor can reconstruct both data of both imaging modalities.

To mechanically integrate the imaging apparatuses 10, 50, the isocenters 22, 62 are preferably aligned on a common gantry axis 66. A prone human subject lying on the subject support couch 18 can be moved parallel to the common gantry axis 66 into one or the other of the bores 16, 56 for imaging using a selected one or both of the imaging apparatuses 10, 50. The rotating gantries 12, 52 rotate about the common gantry axis 66. Preferably, an axial separation of the isocenters 22, 62 along the common gantry axis 66 is calibrated such that after imaging using one apparatus, the subject can be transferred over to the other apparatus and imaged at the same axial position.

Moreover, it will be appreciated that a third, fourth, or more imaging modalities can be similarly integrated in the multiple imaging modality radiological imaging apparatus 8. Each imaging modality includes radiation detectors and radiation sources appropriate to that imaging modality arranged on a rotating gantry inside a toroidal housing that has a cylindrical bore large enough to admit imaging subjects over a range of sizes. It will also be appreciated that, although separate toroidal housings 14, 54 are shown in FIG. 1, a single axially extended toroidal housing could be used which encompasses both imaging apparatuses 10, 50.

Figure 2:
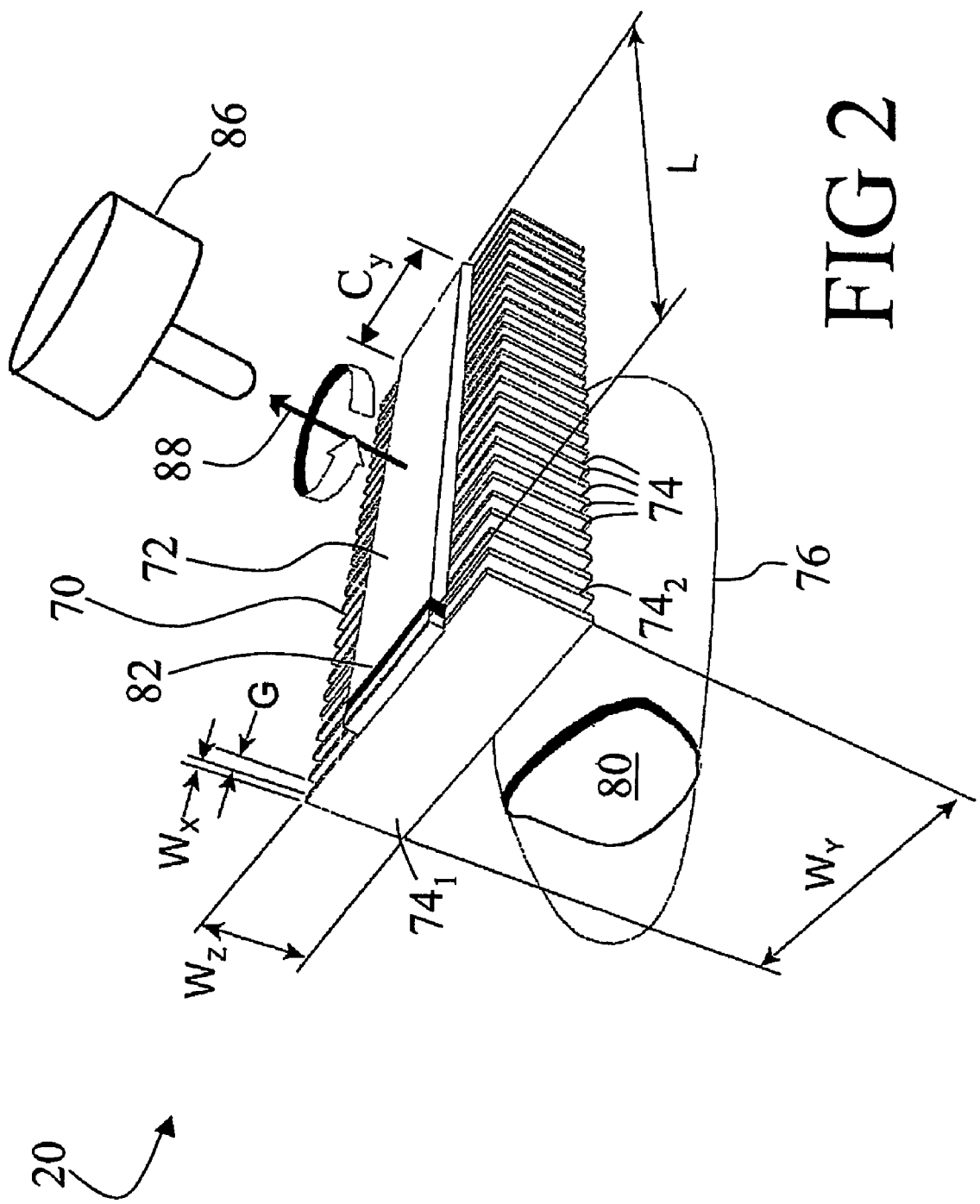
FIG. 2 shows a perspective view of a slat-collimated gamma detector.

With continuing reference to FIG. 1 and with further reference to FIG. 2, imaging is performed using the gamma camera 10 with the gamma detector or detectors 20 at the fixed viewing radius R. To obtain a selected resolution, imaging time, and detection sensitivity at the fixed viewing radius R, a slat-collimated gamma detector 20 is employed, in which a slat collimator 70 and radiation detector 72 are designed to provide the selected resolution, imaging time, and detection sensitivity characteristics. The slat collimator 70 includes a plurality of generally parallel slats 74 of thickness $W_x$ and width $W_y$ separated by gaps G. Each slat has a slat height $W_z$ extending away from the radiation detector 72 toward an imaging region 76. Optionally, the slats tilt uniformly by a few degrees in the same direction.

The radiation detector 72 has dimensions of width Cy parallel to the slats 74, and length L perpendicular to the slats 74. Each adjacent slat pair defines a viewing plane that is generally transverse to the radiation detector 72 and is viewed by a generally linear element array of the radiation detector 72. For example, slats $74_1$, $74_2$ collimate a viewing plane 80 of the imaging region 76. A generally linear radiation detector region 82 of the radiation detector 72 views the plane 80 through the adjacent slats pair $74_1$, $74_2$.

In a preferred embodiment, the radiation detector 72 includes a rectangular array of about 3,000 cadmium zinc telluride (CZT) detector elements each sized at about 3.2 mm×1.8 mm. Each CZT detector element includes an electrically biased photodetector that acquires electrical charge and produces current pulses responsive to incident gamma rays. To provide separable three-dimensional voxel sampling for image reconstruction, the slat-collimated gamma detector 20 is rotated or spun by a rotary motor 86 about a slats rotation axis 88 that is perpendicular to the common gantry axis 66. Typically, for each gantry angular view, plane integral projections are acquired for a 180° or 360° span of slats spin about the slats rotation axis 88.

The fixed viewing radius R is generally substantially larger than an average viewing radius of a conformal gamma detector orbit. As is known in the art, as the viewing distance between the gamma detector and the imaging region increases, imaging resolution degrades. In a conventional gamma detector that employs a bore hole collimator, imaging resolution degradation can be countered by increasing collimation (e.g., by extending the collimator height toward the imaging region or by using smaller collimation openings). However, the increased collimation reduces detector sensitivity by reducing radiation collection efficiency (a higher percentage of radiation is absorbed by the collimator and does not reach the detector). Nuclear cameras heretofore have employed conformal non-circular gamma detector orbits that closely follow external contours of the imaging subject to minimize detector viewing distances and collimation.

The slat-collimated gamma detector 20 is preferably configured for a selected resolution and detector sensitivity over a selected imaging time by independently tailoring resolution via the collimation (e.g., the slat height $W_z$ or the slat separation G) and detector sensitivity via the width $C_y$ of the radiation detector 72. In general, as the gamma detector 20 is moved away from the imaging region 76, the resultant degradation of the imaging resolution is countered by increasing the collimation (e.g., increasing the slat height $W_z$). The detector sensitivity is maintained by increasing the detector width $C_y$ to compensate for the increased viewing distance and collimation. For a selected viewing radius R, imaging resolution, detector sensitivity, and imaging time, optimized values of the collimation and detector width $C_y$ are determined.

More specifically, the imaging resolution generally scales linearly with viewing radius for a given collimation. That is:

$$\text{Imaging resolution} \propto \frac{R}{W_z} \quad (1)$$

where R is the viewing radius R shown in FIG. 1, $W_z$ is the slat height $W_z$ shown in FIG. 2, and a smaller value for the ratio $R/W_z$ corresponds to increased or better imaging resolution. If, for example, a conformal non-circular detector orbit provides a certain imaging resolution at an average viewing radius of 20 cm, then to move to a constant circular detector orbit with a viewing radius of 30 cm (which is sufficient to admit most human subjects in a prone position) without degrading resolution, the height W of the collimator slats 74 should be increased by a factor of (30 cm 20 ÷cm) or 1.5 to provide the same resolution at 30 cm fixed-radius orbit as is obtained using a conformal non-circular orbit with an average radius of 20 cm. Rather than increasing the slat height $W_z$, the slat separation G can instead be decreased to provide the increased collimation at constant radius of 30 cm.

Increasing the viewing radius R reduces detector sensitivity. Furthermore, increasing the collimation also reduces detector sensitivity. For the slat-collimated gamma detector geometry, the detector sensitivity is approximately related to slat height $W_z$ and viewing radius R according to:

$$\text{Detector sensitivity} \propto \frac{1}{W_z^2 + (W_z \cdot R)} \quad (2)$$

where a larger value for Equation (2) corresponds to better detector sensitivity. Hence, for the exemplary increase of the viewing radius from 20 cm to 30 cm and a corresponding proportional increase in slat height $W_z$ of 1.5, the detector sensitivity is proportionately reduced by a factor of 2.25. To compensate for this sensitivity loss, the radiation detector width $C_y$ is suitably proportionally increased by a factor of 2.25.

In summary, the gamma camera 10 of FIG. 1 using the slat-collimated gamma detector 20 illustrated in FIG. 2 provides substantially similar resolution and detector sensitivity at a constant viewing radius R of 30 cm as compared with a conformal gamma camera orbit in which the detector orbits conformally at an average radius of 20 cm. The increased distance from 20 cm to 30 cm is compensated by scaling up the slat height $W_z$ by a factor of 1.5, and by scaling up the detector width $C_y$ by a factor of 2.25. By making these adjustments, imaging at 30 cm fixed radius for a reasonable imaging time, such as about 20 minutes, provides substantially equivalent resolution and detector sensitivity as a 20 minute conformal imaging session at an average viewing radius of about 20 cm. With the conformal orbiting of the gamma detectors eliminated, the enclosing housing 14 is preferably included to improve aesthetic appearance of the gamma camera 10, to be comparable in aspect, shape, and size with other imaging modalities (CT, PET and MRI), to shield the moving gamma detector or detectors 20 and rotating gantry 12 from view, and to prevent contact with moving gamma camera components.

With reference to FIG. 3, another advantage of the constant radius R is that more than three gamma detectors can be simultaneously used for acquiring imaging data. For example, as shown in FIG. 3, four gamma detectors 20 can be mounted on the rotating gantry 12 and simultaneously used for imaging data acquisition. Each of the four detectors 20 is positioned at the viewing distance R from the isocenter 22 of the rotating gantry 12, and so do not interfere with one another. More than four detectors can similarly be employed. In contrast, when a conformal gamma detector orbit such as has been practiced heretofore is used, only three or fewer simultaneously operating gamma detectors is practicable. This is because geometrical constraints substantially hinder conformal non-circular orbiting about an imaging subject by four or more detectors. With four or more conformally non-circularly orbiting detectors, the detectors will generally impinge upon one another at various positions within the orbit. The additional gamma detectors can be used to collect redundant imaging data, or to provide 360° of gantry angular imaging views with a gantry rotation of less than 360°. For the exemplary four detectors 20 shown in FIG. 3, a 90° gantry rotation provides 360° of angular coverage.

With continuing reference to FIG. 3, yet another advantage of the constant radius gamma camera 10 is improved symmetry of the imaging. For example, the four gamma detector arrangement of FIG. 3 has at least a four-fold rotational symmetry and four reflection symmetry planes. This high degree of symmetry can be used to improve radiation detection efficiency, simplify image reconstruction complexity, and reduce image reconstruction time. The inverse distance dependence of slat-collimated plane integral projection views is simplified by the circular orbit since the detector viewing radius R is a constant throughout the detector orbit. As yet another option, additional heads (shown in phantom) can be added to encircle the subject more completely. Increasing the number of detector heads increases counts which improves image quality or reduces data collection time.

With reference to FIG. 4, still yet another advantage slat-collimated gamma detectors orbiting at a constant radius $R_2$ is that the spinning or rotation of the slats 70 about the slats rotation axis 88 can be substantially angularly limited. FIG. 4 shows six gamma detectors $20_1$, $20_2$, $20_3$, $20_4$, $20_5$, $20_6$ spaced at 60° intervals around a rotating gantry 12'. For a 360° rotation of the gantry 12' about the common gantry axis 66, each of the six gamma detectors $20_1$, $20_2$, $20_3$, $20_4$, $20_5$, $20_6$ will traverse every gantry angular view. In other words, for each angular position around the gantry, each of the six gamma detectors $20_1$, $20_2$, $20_3$, $20_4$, $20_5$, $20_6$ views from that angular position at some interval of the 360° gantry rotation. Hence, the 360° spin of the slats about the slats rotation axis 88 is optionally divided among the six gamma detectors $20_1$, $20_2$, $20_3$, $20_4$, $20_5$, $20_6$.

In one suitable arrangement: slats of gamma detector $20_1$ spin between 0° and 60°; slats of gamma detector $20_2$ spin between 60° and 120°; slats of gamma detector $20_3$ spin between 120° and 180°; slats of gamma detector $20_4$ spin, between 180° and 240°; slats of gamma detector $20_5$ spin between 240° and 300°; and slats of gamma detector $20_6$ spin between 300° and 360°, all around the slats rotation axis 88. Because the spinning of the slats about the axis 88 for each gamma detector spans only 60°, the rotary motor 86 shown in FIG. 2 can be replaced by a linear arm actuator, which simplifies mechanical construction of the slat-collimated gamma detectors.

With returning reference to FIG. 1, the multiple imaging modality radiological imaging system 8 provides SPECT imaging through the gamma camera 10 and another imaging modality such as PET or CT through the second imaging modality apparatus 50. For a calibrated separation of the isocenters 22, 62 of the two rotating gantries 12, 52, switching between the two imaging modalities can be rapidly and conveniently performed by calibrated axial movement of the patent support 18. However, it Dial separation of the gantries 12, 52 precludes simultaneous imaging at the same axial position using the two imaging modalities.

With reference to FIG. 5, a gantry 12" provides simultaneous SPECT and second-modality imaging at the same axial position. Four SPECT gamma detectors 20' are arranged on a circular rotating gantry 12" at a viewing distance $R_3$ from a gantry isocenter 22". This arrangement is substantially similar to the arrangement of gamma detectors 20 on the rotating gantry 12 shown in FIG. 3. The fixed-radius circular orbiting of the SPECT gamma detectors 20' enables interleaving of additional radiation detectors 94 between the SPECT gamma detectors 20' on the rotating gantry 12". In FIG. 5, four PET detectors 94 are arranged on the gantry 12", viewing the isocenter 22" at a distance $R_4$ which may be the same as or different from the viewing distance $R_3$ of the SPECT gamma detectors 20'. The uncollimated PET detectors 94 suitably acquire coincidence PET data simultaneously with acquisition of SPECT data by the gamma detectors 20'.

With reference to FIG. 6, in a similar fashion, a computed tomography scanner is integrated onto a fixed-radius gamma camera employing slat-collimated detectors 20" arranged on a gantry 12''' about an imaging isocenter 22''' at a viewing radius $R_5$. The computed tomography scanner includes an x-ray source 96 and an oppositely disposed x-ray detector array 98. In the single-gantry SPECT/CT system, simultaneous acquisition of SPECT data and CT data is complicated by a large difference in optimal rotation rates for the CT and SPECT imaging modalities, different radiation intensities, scattered radiation, and the like. However, the preferred CZT detectors 72 of the slat-collimated SPECT gamma detectors 20" are advantageously resistant to damage by scattered high-intensity x-rays when they are shut off, and so SPECT and CT can be acquired sequentially without moving the subject support 18 and without shuttering the SPECT gamma detectors 20" during operation of the x-ray tube 96. Alternatively, the source 96 can be an isotope source.

Other imaging modalities can be similarly integrated onto a single constant-radius SPECT gantry. For example, dissimilar gamma detectors or differently collimated gamma detectors can be interleaved on the gantry to provide different imaging resolutions, differently optimized spectral characteristics, or the like. Similarly, a transmission-mode SPECT system including a suitable gamma radiation source and dedicated receiving gamma detector can be integrated onto the gantry.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A nuclear camera capable of performing SPECT imaging, the nuclear camera including:
   a generally circular rotatable gantry defining a gantry rotation axis and an imaging isocenter; and
   a gamma detector arranged on the generally circular rotating gantry at a constant fixed radial distance from the imaging isocenter to circularly and non-conformally orbit the imaging isocenter at the constant fixed radial distance, the gamma detector including a radiation-sensitive surface and a collimator that collimates incoming radiation.

2. The nuclear camera as set forth in claim 1, wherein the collimator includes:
   a plurality of spaced apart slats arranged transverse to the radiation sensitive surface, each adjacent slat pair defining a viewing plane.

3. The nuclear camera as set forth in claim 2, wherein the gamma detector further includes:
   a means for spinning the collimator slats and the radiation sensitive surface about a slat rotation axis that is generally orthogonal to the gantry rotation axis.

4. The nuclear camera as set forth in claim 3, wherein:
   the slats have a spacing and height selected based on a selected spatial imaging resolution, a predetermined imaging time, and the fixed radial distance; and
   a width of the radiation sensitive surface parallel to the slats is selected based on a selected detector sensitivity, the predetermined imaging time, the fixed radial distance, and the slat pair.

5. The nuclear camera as set forth in claim 4, wherein the slat height in a direction transverse to the radiation sensitive surface corresponds to a ratio of the fixed radial distance and the selected spatial imaging resolution.

6. The nuclear camera as set forth in claim 3, wherein the radiation sensitive surface includes an array of solid state detector elements.

7. The nuclear camera as set forth in claim 6, further including:
   a radiation source disposed on the rotatable gantry and producing transmission radiation; and
   an transmission radiation detector mounted opposite the radiation source that detects the transmission radiation.

8. The nuclear camera as set forth in claim 1, further including at least four gamma detectors mounted at the fixed radial distance from the imaging isocenter.

9. The nuclear camera as set forth in claim 8, further including:
   at least a pair of radiation detectors oppositely mounted on the rotatable gantry that are configured to perform coincidence detection of radiation emitted during positron electron annihilation.

10. The nuclear camera as set forth in claim 8, wherein the:
    the gamma detectors are collimated for at least two different imaging resolutions.

11. A nuclear camera including:
    at least four SPECT radiation detectors rotatably arranged around an imaging region to receive emission radiation, the radiation detectors each disposed an equal constant fixed distance from an imaging isocenter, the radiation detectors each including a radiation sensitive surface;
    a slat collimator disposed on each radiation detector between the radiation detector and the imaging region to provide planar collimation of incoming emission radiation:
    a means for s spinning the collimator and radiation sensitive surface of each SPECT radiation detector about a detector axis; and
    a generally circular rotatable gantry on which the radiation detectors are disposed; and
    an optically opaque toroidal housing that is substantially transmissive for the first emission radiation.

12. The nuclear camera as set forth in claim 11, further including radiation detectors configured for at least one of a different SPECT resolution and a different imaging modality.

13. The nuclear camera as set forth in claim 11, further including:
    a computed tomography scanner including a transmission radiation source and a transmission radiation detector disposed opposite the transmission radiation source on the rotatable gantry.

14. A radiological imaging method including:
    circularly orbiting at least one radiation detector about an imaging volume at a fixed radial distance from a first axis of rotation through the imaging volume;
    detecting radiation from the imaging volume at a generally planar radiation sensitive region of the radiation detector, the radiation sensitive region facing the imaging volume during the fixed radius circular orbiting;
    during the circular orbiting, spinning a slat collimator and a radiation sensitive array about an axis perpendicular to the first axis of rotation, wherein the orbiting rotates each of a plurality of detectors to common locations M times, where M is an integer greater than one, and the collimator and radiation sensitive array are spun one of 180°/M and 360°/M at each location;
    integrating radiation detected over generally planar regions defined by the slat collimator to generate plane integral projection views; and
    reconstructing an image representation of the imaging volume from the plane integral projection views.

15. The radiological imaging method as set forth in claim 14, further including:
    selecting a minimum width of the generally planar radiation sensitive array in a direction parallel to the generally planar regions to provide a selected radiation detection sensitivity.

16. The radiological imaging method as set forth in claim 14, further including:
    selecting at least one of collimator slat spacing and collimator height in accordance with a selected resolution and the fixed radial distance.

17. The radiological imaging method as set forth in claim 14, further including:
    disposing a radiation transmissive, optically opaque shield between the at least one radiation detector and the imaging volume, the shield remaining stationary during the circular orbiting and blocking optical communication between the imaging volume and the radiation detector during the circular orbiting.

18. The radiological imaging method as set forth in claim 14, further including:
    orbiting at least four radiation detectors at the fixed radial distance.

19. The radiological imaging method as set forth in claim 18, wherein the detectors include SPECT detectors collimated for a first resolution and at least one of:
- a SPECT detector collimated for a second resolution,
- a pair of PET detectors, and
- a transmission radiation detector.

20. An imaging apparatus comprising:
- a circular rotatable gantry defining a gantry rotation axis and an imaging isocenter;
- three or more gamma detectors arranged on the circular rotatable gantry at a fixed radial distance from the imaging isocenter;
- a collimator located on each of said three or more gamma detectors; and
- a means for processing data detected by said three or more gamma detectors to produce an image.

21. The imaging apparatus of claim 20 wherein each of the collimators includes a plurality of spaced-apart slats and a means for spinning the collimator slats about a slat rotation axis.

22. An imaging apparatus comprising:
- at least four SPECT radiation detectors rotatably arranged around an imaging region, each detector disposed at an equal fixed and non-adjustable distance from an imaging isocenter, such that each detector can rotate completely around the imaging region while being fixed at the fixed and non-adjustable distance from the imaging isocenter, wherein each detector includes:
- a slat collimator, wherein at least one of collimator slat spacing and collimator height arc selected to provide a predetermined resolution at said fixed distance; and
- a detector width selected to provide a predetermined radiation detection sensitivity at said fixed distance.

23. The imaging apparatus of claim 22 wherein each slat collimator includes a plurality of spaced-apart slats and a means for spinning the collimator slats about a slat rotation axis.

* * * * *